United States Patent
Noonan et al.

(10) Patent No.: US 9,877,796 B2
(45) Date of Patent: Jan. 30, 2018

(54) SYSTEM AND METHOD FOR MINIMIZING FIBER TWIST IN OPTICAL SHAPE SENSING ENABLED DEVICES

(71) Applicant: KONINKLIJKE PHILIPS N.V., Eindhoven (NL)

(72) Inventors: David Paul Noonan, New York, NY (US); Bharat Ramachandran, Morganville, NJ (US); Raymond Chan, San Diego, CA (US); Molly Lara Flexman, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/917,975

(22) PCT Filed: Sep. 10, 2014

(86) PCT No.: PCT/IB2014/064367
§ 371 (c)(1),
(2) Date: Mar. 10, 2016

(87) PCT Pub. No.: WO2015/044815
PCT Pub. Date: Apr. 2, 2015

(65) Prior Publication Data
US 2016/0206396 A1    Jul. 21, 2016

Related U.S. Application Data (60) Provisional application No. 61/884,157, filed on Sep. 30, 2013.

(51) Int. Cl.
*G01B 11/24*    (2006.01)
*A61B 90/00*    (2016.01)
(Continued)

(52) U.S. Cl.
CPC .............. *A61B 90/36* (2016.02); *A61B 34/20* (2016.02); *G01B 11/24* (2013.01); *G02B 6/36* (2013.01); *A61B 2034/2061* (2016.02)

(58) Field of Classification Search
CPC . A61B 90/36; A61B 34/20; A61B 2034/2061; G01B 11/24; G02B 6/36
(Continued)

(56) References Cited

U.S. PATENT DOCUMENTS

| 4,753,501 A | * | 6/1988 | Battle | .................. G02B 6/3504 385/22 |
|---|---|---|---|---|
| 7,035,525 B2 | | 4/2006 | Weeks | |

(Continued)

FOREIGN PATENT DOCUMENTS

| CN | 102892347 A | 1/2013 |
|---|---|---|
| WO | 0133184 A1 | 5/2001 |

OTHER PUBLICATIONS

Yan, Z. et al., "All-fibre twist sensor system based on 45 degrees and 81 degrees tilted fibre gratings", 21st International Conference on Optical Fiber Sensors, SPIE, vol. 7753, 77538E, 2011.

*Primary Examiner* — Tri T Ton (57) ABSTRACT

A fiber twist reduction system for optical shape sensing enabled instruments includes a rotatable launch fixture (12) configured to hold an optical fiber (28). An optical shape sensing enabled device (26) includes the optical fiber disposed therein. A rotation mechanism (14) is configured to rotate the fiber in response to a twist of the fiber to reduce accumulated twist along its length.

15 Claims, 4 Drawing Sheets

(51) Int. Cl.
*G02B 6/36* (2006.01)
*A61B 34/20* (2016.01)

(58) Field of Classification Search
USPC ............ 356/614–615, 625–640; 56/601–613
See application file for complete search history.

(56) References Cited

U.S. PATENT DOCUMENTS

| | | |
|---|---|---|
| 2004/0062514 A1 | 4/2004 | Weeks et al. |
| 2007/0156019 A1 | 7/2007 | Larkin et al. |
| 2011/0172680 A1 | 7/2011 | Younge et al. |
| 2011/0202069 A1 | 8/2011 | Prisco et al. |
| 2012/0281205 A1 | 11/2012 | Askins |
| 2012/0321243 A1 | 12/2012 | Younge et al. |

* cited by examiner

SYSTEM AND METHOD FOR MINIMIZING FIBER TWIST IN OPTICAL SHAPE SENSING ENABLED DEVICES

CROSS-REFERENCE TO PRIOR APPLICATIONS

This application is the U.S. National Phase application under 35 U.S.C. §371 of International Application Serial No. PCT/IB2014/064367, filed on Sep. 10, 2014, which claims the benefit of U.S. Application Ser. No. 61/884,157, filed on Sep. 30, 2013. These applications are hereby incorporated by reference herein.

BACKGROUND

Technical Field

This disclosure relates to medical instruments and more particularly for reducing twist in shape sensing optical fibers in medical applications.

Description of the Related Art

Shape sensing based on fiber optics exploits the inherent backscatter in a conventional optical fiber. The principle used is distributed strain measurement in the optical fiber with characteristic Rayleigh scatter patterns, for example, in standard single-mode communications fiber. Rayleigh scatter occurs as a result of random fluctuations of the index of refraction in the fiber core. These random fluctuations can be modeled with a random variation of amplitude and phase along the length. Fiber Bragg gratings may also be employed. By using these effects in 3 or more cores running within a single length of multicore fiber, three-dimensional (3D) shape and dynamics of a surface of interest can be reconstructed.

With a 4 or more core fiber system where one core is located in the center of the cross-section, one is able to separate strain due to bending and temperature effects as long as no axial strain (tension) is applied, or if the tension is known and controllable (or can be calibrated out). Reference files store values (also called wobble) of a rate of windings of the outer cores around the central core, but when there is excessive twist, it becomes more difficult to distinguish this effect since the rate of change of the wobble increases at a non-linear rate. This often leads to inaccuracy beyond $2\pi$ torsion and instability beyond $6\pi$ torsion about the fibers longitudinal axis.

Integrating a fiber into a fixed tip Optical Shape Sensing (OSS) enabled device involves fixing a launch region of the fiber within a launch fixture, and the tip of the fiber within a distal tip of an instrument. Assuming that the launch fixture is attached rigidly to an operating table or other structure, these two fixation points will result in an accumulation of twist along the length of the fiber as the instrument is torqued during an intervention. Knowledge of this twist value is used to measure the roll degree of freedom of the instrument. However, the OSS fiber can only produce accurate shape reconstruction until approximately $2\pi$ twist about its axis in either direction, losing stability close to $6\pi$ of cumulative twist.

Twist can be introduced by the operator rotating the instrument during manipulation or, by friction between the fiber and the instrument lumen (stick-slip) as the instrument is moved. During clinical use, specifically in vascular procedures, physicians often rotate (or 'torque') a guidewire/instrument through multiple $\pi$ turns. Such torquing leads to a build-up of twist in fixed-tip devices, which although necessary to measure the orientation of the device, causes shape sensing to lose accuracy, then stability and finally causing breakdown of shape reconstruction. This limitation severely impacts the clinical usability of fixed tip OSS devices as it imposes restrictions on the clinician. Hence, it is essential to minimize the amount of twist which is imparted on the fiber by the clinician, while ensuring that the orientation of the instrument is still known and the instrument can still be operated and torqued in the usual manner.

SUMMARY

In accordance with the present principles, a fiber twist reduction system for optical shape sensing enabled instruments includes a rotatable launch fixture configured to hold an optical fiber. An optical shape sensing enabled device includes the optical fiber disposed therein. A rotation mechanism is configured to rotate the fiber in response to a twist of the fiber to reduce accumulated twist along its length.

A fiber twist reduction system for optical shape sensing enabled instruments includes an optical shape sensing enabled device having at least one optical fiber disposed therein. A rotatable launch fixture is configured to hold the at least one optical fiber, and a rotation mechanism is configured to rotate a launch region of the at least one optical fiber. A controller is coupled to the rotation mechanism and configured to enable the rotation mechanism in response to a twist of the at least one optical fiber to at least reduce accumulated twist within the at least one optical fiber.

A method for reducing accumulated twist in an optical fiber for a shape sensing enabled device includes providing a rotatable fiber launch fixture being configured to hold at least one optical fiber, an optical shape sensing enabled device including the at least one optical fiber disposed therein, and a rotation mechanism configured to rotate the optical fiber disposed in the rotatable fiber launch fixture; measuring a twist in the at least one optical fiber disposed within the optical shape sensing enabled device; and, in response to the twist, rotating the fiber launch fixture using the rotation mechanism to at least reduce accumulated twist within the at least one optical fiber.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, an apparatus and method are provided for measuring and accounting for twist in an optical shape sensing (OSS) device using, e.g., a single degree of freedom actuated launch fixture. The fixture manipulates a launch region of an OSS fiber to minimize accumulated twist along the length of the fiber. In one embodiment, the apparatus includes a motor, an encoder, a motor controller and a mechanism suitable for rotating the launch region along the axis of the fiber. Twist is minimized by closing a motor control loop with the twist signal from the fiber, such that as an accumulation of twist is observed in the fiber, the motor will rotate the launch region to drive the twist value to zero.

Since this rotation will effectively also change the coordinate system of the fiber reconstruction (e.g., it will cause a rotation about the z-axis of the fiber, i.e., along its longitudinal axis), an encoder is needed to measure the absolute angular displacement which the launch region undergoes so that the fiber's shape and orientation can be accurately reconstructed within the correct frame of reference. A single degree of freedom (1-DoF) mechanism is actuated to minimize twist accumulation in fixed tip devices, while also allowing for the roll degree of freedom of the device to be measured. Robotic or mechatronic mechanisms may be employed that move a launch/proximal segment of the fiber in a twist minimizing manner as described.

Hence, the present principles minimize the amount of twist imposed on the fiber by the clinician, while ensuring that the orientation of the instrument is still known. The instrument can still be operated and torqued in the usual manner by a clinician. Various embodiments may include robotic/mechatronic mechanisms that move the launch/proximal segment of the fiber in a twist minimizing manner.

It also should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
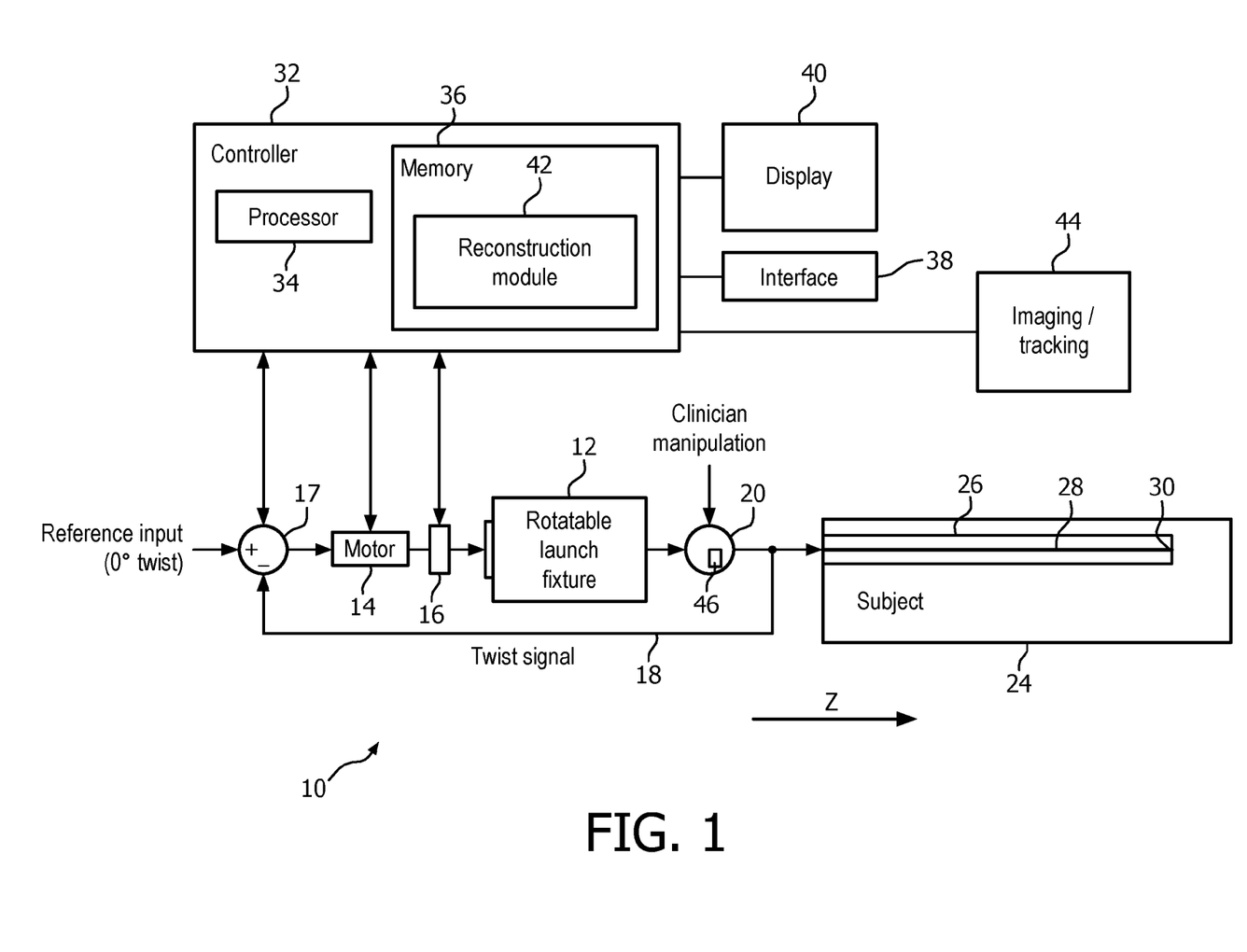
FIG. 1 is a block/flow diagram showing a shape sensing system having a rotatable launch fixture and controls in accordance with illustrative embodiments.

Referring now to the drawings in which like numerals represent the same or similar elements and initially to FIG. 1, an optical shape sensing launch system 10 is illustratively shown in accordance with one embodiment. The system 10 includes a rotatable launch fixture 12. The rotatable launch fixture 12 includes a single degree of freedom actuated component which can be rigidly attached or mounted to an operating table or other structure and is employed to hold an optical fiber 28 and/or an instrument 26 including the optical fiber 28 in place. Launch fixtures typically do not have any rotating components. However, in accordance with the present principles, the rotatable launch fixture 12 has a launch region of the OSS fiber bonded or otherwise affixed thereto. The rotatable launch fixture 12 rotates with respect to the remainder of the launch system 10 to minimize twist in an OSS instrument or device 26.

The launch region include a longitudinal distance along (e.g., approximately 20 mm) the fiber 28 from which the reconstruction starts. This defines the (0,0,0) position of the fiber 28. The launch region is provided such that a reconstruction module or algorithm 42 has a 20 mm length with linear strain in order to initialize the reconstruction. Since the reconstruction starts from the launch region, the position and orientation of the launch region needs to be known throughout a procedure so that any pre-operative registrations performed remain valid.

The fixture 12 manipulates the launch region of the fiber or fibers 28 on the OSS enabled device or instrument 26 to minimize the accumulated twist along the length of the fiber 28. The system 10 may include a motor 14 or similar device, a sensing device, such as, an encoder 16, and a motor controller 32. An error minimization component 17 may be included to reference a zero twist position for the controller 32, and a mechanism or handle 20 may be provided suitable for rotating the launch region of the fiber 28.

The rotating launch fixture 12 includes a groove or other mechanism for fixing the launch region of the optical fiber 28 in place. Since the launch region of the fiber 28 is the location along the fiber from which the shape reconstruction starts and defines the initial position and orientation of any reconstructed shape (i.e., the (0,0,0) position of the fiber), it is preferable that the entire launch region be secured in the launch fixture 12.

Twist is minimized by closing the motor control loop with a twist signal 18 from the fiber 28 or other source (e.g., imaging and/or tracking systems 44) such that as an accumulation of twist is observed in the fiber 28, the motor 14 will rotate the rotatable launch fixture 12, and hence the launch region of the fiber to drive the twist value to zero. In one embodiment, the entire launch system 10 may be made to rotate, not just a rotatable element within the launch fixture 12.

Since the rotation will effectively also change the coordinate system of the fiber reconstruction (i.e., it will cause a rotation about the z-axis of the fiber), an encoder 16 is employed to measure the absolute angular displacement which the fiber launch region undergoes so that the fiber's shape and orientation can be accurately reconstructed within the correct frame of reference. The twist signal 18 from the OSS fiber 28 is input to the motor controller 32. The controller 32 employs the twist signal as feedback to rotate the fiber launch region to minimize the twist experienced by the fiber 28. Measurement of this rotation can then be used as an input to the fiber reconstruction algorithm or module 42 stored in memory 36. An encoder signal from the encoder 16 is provided to the motor controller 32 and can be interfaced with the fiber reconstruction algorithm 42 to ensure the coordinate system is updated for collecting future data in accordance with any movement of the fixture 12 and fiber 28.

It should be understood that the motor controller 32 may include a separate or stand-alone controller or may be part of a computer system or OSS console, which provides other functions such as fiber shape reconstruction, user enabled programming, user interfacing, etc. For example, the controller 32, system 10 and other features may be part of a workstation or console from which a procedure is supervised and/or managed.

The controller 32 may include one or more processors 34 and memory 36 for storing programs and applications. Memory 36 may store the fiber reconstruction algorithm or module 42, which is configured to interpret optical feedback signals from the OSS enabled device 26. Module 42 is configured to use the optical signal feedback to reconstruct deformations, deflections and other changes associated with the OSS enabled device, which may include a medical device or instrument. Twist is minimized by closing the motor control loop with the twist signal 18 from the fiber 28, such that as an accumulation of twist is observed in the fiber 28, the motor 14 will rotate the launch region to drive the twist value to zero. The twist signal 18 may be processed from the OSS console or controller 32 or can be interfaced with the actuated rotatable launch fixture 12 using standard methods such as a TCP/IP communication channel or an EEPROM which is overwritten every time the motor 14 reads from it, etc. Other signals representing generated twist in the fiber 28 may also be employed for these or other devices or modules.

In another embodiment, the rotation of the fiber launch region may be achieved by passive rather than actuated means. In such an embodiment, the rotation of the instrument 26 induced by the operator is mechanically coupled to the rotatable launch fixture 12. The rotatable launch fixture 12 may be rotated along with the handle 20 to prevent twist accumulation. In another embodiment, the mechanism to rotate the fiber 28 may not be located within the launch fixture 12, but rather may be located at some point along the length of the instrument 26. In such an embodiment, the mechanism could be located within the handle 20 or hub along the length of the instrument 26.

The OSS enabled device 26 may include a catheter, a guidewire, a probe, an endoscope, a robot, an electrode, a filter device, a balloon device, or other medical component, etc. The OSS enabled device 26 may include one or more optical fibers 28 which are coupled to the device 26 in a set pattern or patterns. The optical fibers 28 connect to the rotating launch fixture 12. OSS enabled device 26 may have its shape and/or position determined using, e.g., fiber optic Bragg grating sensors, Rayleigh scattering or other scattering.

A shape image or other output may be viewed on a display 40. The display 40 may be configured for viewing internal images of a subject (patient) or volume 24 and may include the image as an overlay or other rendering of the sensing device 26. Display 40 may also permit a user to interact with the controller 32 and its components and functions, or any other element within the system. This is further facilitated by an interface 38 which may include a keyboard, mouse, a joystick, a haptic device, or any other peripheral or control.

In accordance with the present principles, accumulated twist is minimized in a fixed-tip OSS enabled instrument 26 by rotating the launch region of the fiber 28 to keep the twist signal at or close to zero. In another embodiment, the launch region may be rotated based on a measurement of a change in twist over time (instead of the overall time). In this way, rotation corrections can be made more gradual and/or controlled.

Other methods or mechanisms to rotate the launch region may be employed and may include different OSS enabled devices, actuated mechanisms including rotational motor(s), encoder(s), bearing(s), transmission element(s), linear actuator(s), motor controller(s), etc. In one embodiment, an EEPROM can be used to store the OSS fiber parameters and motor angular and linear displacements.

In other embodiments, different inputs may be used to close the control loop when an OSS or twist signal 18 is not available or useable. Replacement signals for the OSS twist data may include the use of an imaging system (camera, x-ray, etc.) and/or tracking system (infrared (IR)/optical/electromagnetic (EM)) 44 which tracks the instrument or clinician's hand as they manipulate the device 26. In another embodiment, a separate rotational encoder 46 may be included within the handle 20 (or hub, torque or launch fixture) which measures the torque or twist applied to the instrument by the operator. In yet another embodiment, a twist calculation based on changes in orientation of the known shape of the instrument may be employed. This shape information could be obtained from OSS or other imaging modalities (x-ray, for example). In these alternate scenarios, the proximal rotation by the operator is correlated with the accumulated twist at a distal tip 30. This may include an instrument specific calibration to identify the effectiveness of the torque transmission of the instrument. Thus, by measuring the rotation at the proximal end, the rotation at the distal tip 30 can be approximated, the accumulated twist calculated and the fiber rotated appropriately to compensate.

While the present principles are applicable for use during interventional procedures (e.g., in all endovascular and endoluminal applications), the present embodiments may be employed for other uses as well. For example, the system 10 may be employed during integration of the fiber 28 (within the device 26) at an end of a device manufacturing line to ensure the device 26 is shipped in a minimum twist configuration. Another use includes calibration of twist in the device 26 after integration and/or before clinical use. In this way, a low twist state can be achieved prior to the procedure or prior to fixation of the tip 30 of the fiber 28 during integration. This will also permit the setting of the twist thresholds specific to the device 26 employed during a procedure, for example, to indicate to the operator that the twist limit of the fiber is approaching.

Figure 2:
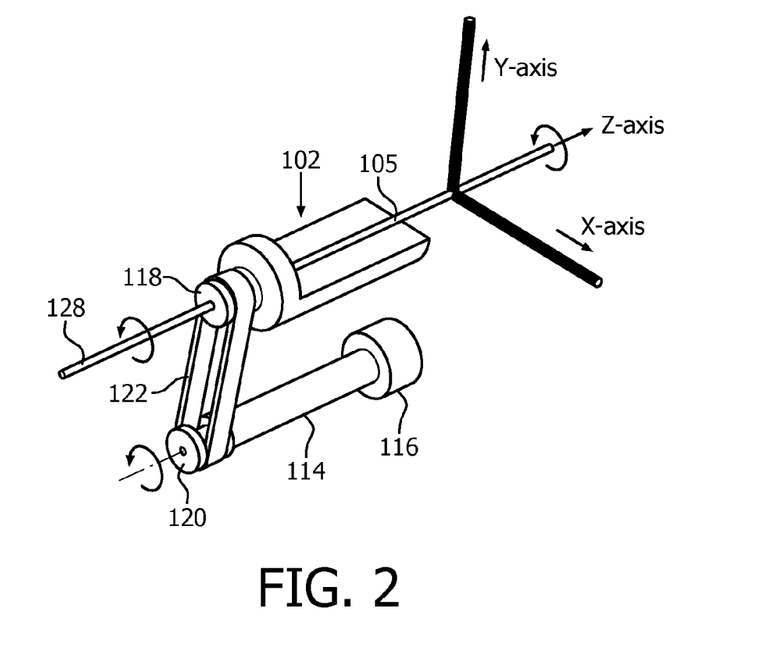
FIG. 2 is a perspective view of a default position of the rotatable launch fixture in accordance with an illustrative embodiment.

Referring to FIG. 2, an example configuration of an actuated launch fixture 102 is shown in accordance with one embodiment. A motor 114 and an absolute encoder 116 are coupled to the launch fixture 102 via two capstans 118, 120 and a belt 122 or other torque transfer mechanism (element) (e.g., gears, wheels, etc.). The launch fixture 102 includes a fiber 128 or fibers for an OSS enabled device. A launch region 105 of the fiber or fibers is rigidly attached to the launch fixture 102. When the motor 114 rotates, the launch fixture 102 and consequently the fiber 128 rotate. In practice, as the clinician torques the OSS enabled device or instrument, the OSS system (e.g., module 42, FIG. 1) (through the fiber 128) would register an increase in twist. This twist would be minimized by rotating the launch region 105 in the same direction as the twist to ensure a 'zero" net twist along the length of the fiber 128. The absolute encoder 116 is employed to update an orientation of the OSS enabled device within the reconstruction algorithm or module 42. In the example of FIG. 2, the rotating launch fixture 102 is turned using the belt 122, which is caused to rotate by the motor 114. The encoder 116 is used to identify the absolute angular displacement of the launch region 105 so that the fiber shape can be reconstructed accurately in the correct frame of reference.

Actuation by the motor 114 can be achieved using a brushed DC, a brushless DC, pneumatic, ultrasonic, piezoelectric or similar motors or servos. An angular velocity achievable by the rotation of the launch fixture 102 should be greater than the maximum rate of rotation expected during clinical rotation. The absolute encoder 116 or other sensing mechanism may include absolute or incremental optical, magnetic, potentiometric or similar encoding schemes. In some embodiments, a differential twist signal from the fiber 128 can be used to identify the absolute angular displacement of the launch region 102 from the zero position over time.

In another embodiment, robotic actuation may be employed to include translations in the X, Y and Z directions. In particular, translation along the Z axis of the fiber 128 could be used to address stick-slip of the fiber 128 within its lumen. This stick slip feature is identified by jumps in the twist signal as measured from the fiber.

Clinicians are typically unable to manipulate fixed tip OSS-enabled devices through multiple turns without causing twist accumulation. This accumulation in twist leads to reconstruction inaccuracies and ultimately a complete loss of shape. The present embodiments minimize the accumulated twist within fixed tip OSS enabled devices, and permit for accurate shape reconstruction without the need for manipulation restrictions to be imposed on an operating clinician.

Figure 3:
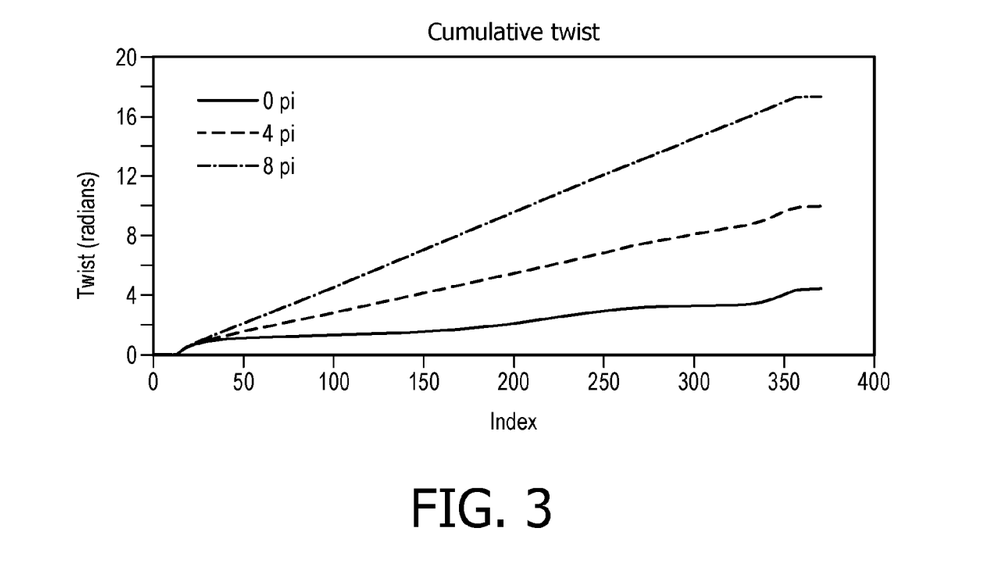
FIG. 3 is a graph showing cumulative twist by plotting twist (radians) versus index count for an optical shape sensing device with a fixed tip.

Referring to FIG. 3, a graph illustrates twist accumulation in an OSS fiber when the distal tip of a fiber is rotated through both $4\pi$ (4pi) and $8\pi$ (8pi) while the launch region remains fixed. An unrotated trace (0pi) is also shown. The graph clearly shows that the maximum twist value increases from 4 radians to 18 radians as the tip is rotated.

Figure 4:
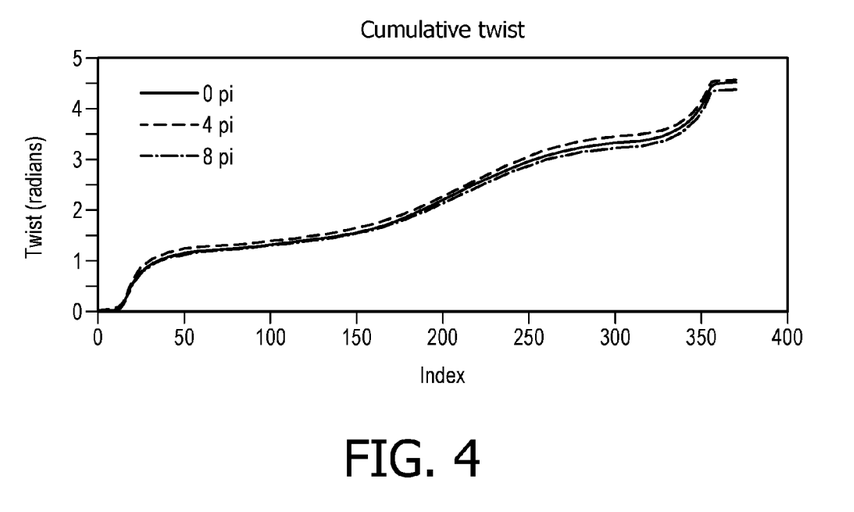
FIG. 4 is a graph showing cumulative twist by plotting twist (radians) versus index count for an optical shape sensing device with a fixed tip having twist compensation in accordance with the present principles.

Referring to FIG. 4, a graph illustrates twist accumulation in an OSS fiber when both the distal tip and the launch region are rotated through $4\pi$ (4pi) and $8\pi$ (8pi) rotations in the same direction. An unrotated trace (0pi) is also shown. In this case, the level of accumulated twist does not change (remains constant), thus clearly demonstrating that the overall twist value can be managed by rotating the launch region to match the rotation experienced by the tip.

Figure 5:
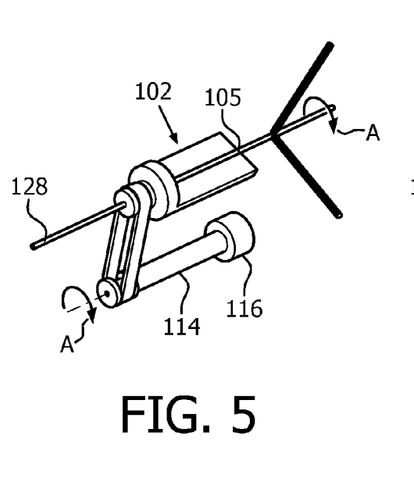
FIG. 5 is a perspective view of the rotatable launch fixture showing a twist compensated for in a first direction in accordance with an illustrative embodiment.
Figure 6:
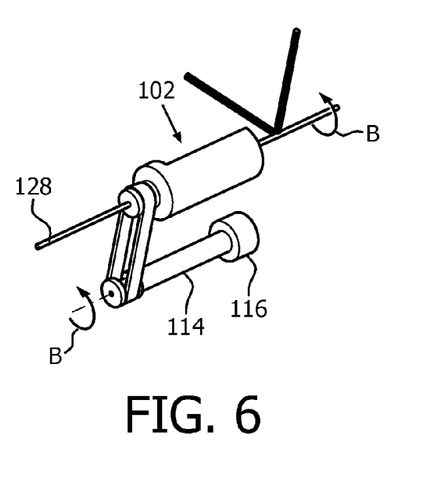
FIG. 6 is a perspective view of the rotatable launch fixture showing a twist compensated for in a second direction in accordance with an illustrative embodiment.

Referring to FIGS. 5 and 6 with continued reference to FIG. 2, FIG. 2 shows a default position for the launch fixture 102. When the motor 114 rotates clockwise (arrow A) so too does the launch fixture 102 and fiber 128, thus changing the orientation of the fiber (FIG. 5). FIG. 5 shows rotation of the launch fixture 102 through +30° to account for a +30° rotation of the instrument (and hence the fiber 128) by a clinician. When the motor 114 rotates counter-clockwise (arrow B, FIG. 6) so too does the launch fixture 102 and fiber 128. This also changes the orientation of the fiber 128. FIG. 6 shows a rotation of the launch fixture 102 through −90° to account for a −90° rotation of the instrument (and hence the fiber 128) by the clinician.

In practice, as the clinician torques the instrument, the OSS system (controller 32) registers an increase in twist. This twist would be minimized by rotating the launch region in the same direction as the twist to ensure zero net twist along the length of the fiber 128. The absolute encoder 116 would be used to update the orientation of the device within the reconstruction algorithm (42, FIG. 1). Note that this rotation of the fiber 128 would occur without causing a rotation of the instrument in which the fiber 128 is stowed.

The belt 122 causes rotation of the launch fixture 102 and consequently the fiber launch region (105, FIG. 5). The encoder 116 is employed to identify the absolute angular displacement of the launch region 105 so that the fiber shape can be reconstructed accurately in the correct frame of reference.

Figure 7:
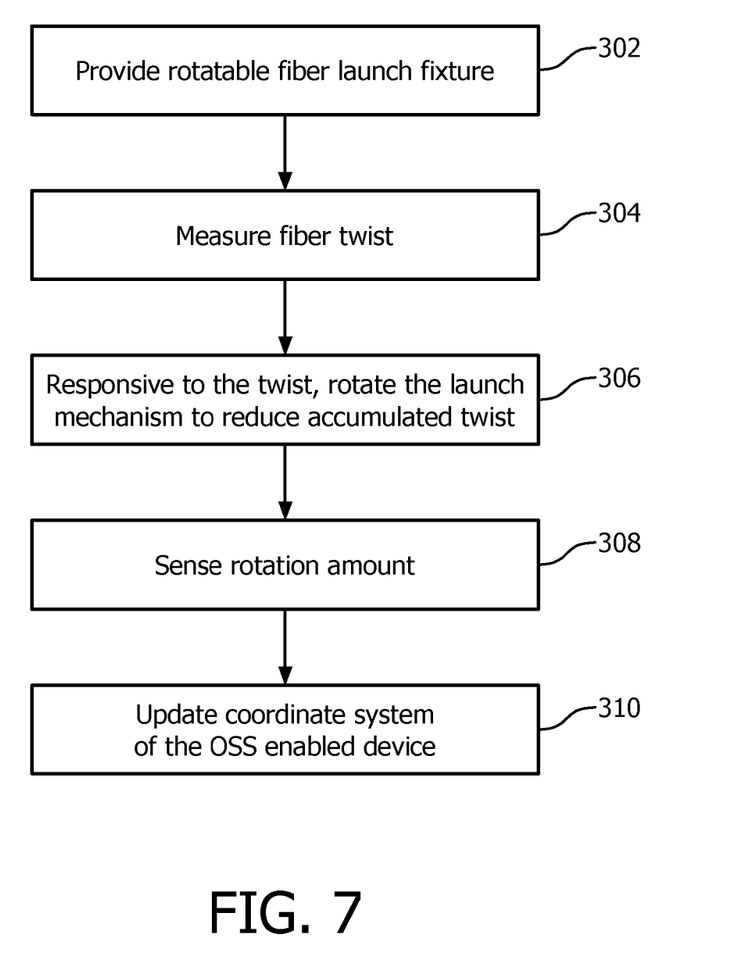
FIG. 7 is a flow diagram showing a method for accumulated twist reduction in an optical shape-sensing fiber in accordance with an illustrative embodiment.

Referring to FIG. 7, a method for reducing accumulated twist in an optical fiber is shown. In block 302, a launch fixture is configured to a rotate a fiber launch region. The fixture is configured to hold at least one optical fiber. An optical shape sensing enabled device includes the at least one optical fiber, which is disposed therein. A rotation mechanism, such as a motor is configured to rotate the launch fixture and therefore the launch region. In block 304, a twist is measured in the at least one optical fiber disposed within the optical shape sensing enabled device. In block 306, in response to the twist, the launch region is rotated in the fixture using the rotation mechanism to at least reduce accumulated twist within the at least one optical fiber. The rotation mechanism may include a motor configured to be responsive to the twist in the at least one optical fiber. The rotation mechanism may be responsive to optical shape sensing signals indicating the twist in the at least one optical fiber, and/or may be responsive to an imaging system and/or a tracking system. The imaging and/or tracking system is independent from shape sensing system of the optical shape sensing enabled device. The imaging system and/or the tracking system may be employed to indicate the twist in the at least one optical fiber.

In block 308, rotation of the launch fixture is sensed. In block 310, a coordinate reference of the optical shape sensing enabled device is updated based on the rotation.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for minimizing fiber twist in optical shape sensing enabled devices (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A fiber twist reduction system for optical shape sensing enabled instruments, the system comprising:
    a rotatable launch fixture configured to hold at least one optical fiber;
    an optical shape sensing enabled device including the at least one optical fiber disposed therein; and
    a rotation mechanism configured to rotate the at least one optical fiber by rotating the rotatable launch fixture in response to a twist in the at least one optical fiber to reduce accumulated twist along a length of the at least one optical fiber.

2. The system as recited in claim 1, wherein the rotation mechanism includes a motor configured to be responsive to the twist in the at least one optical fiber.

3. The system as recited in claim 2, wherein the motor is configured to be responsive to optical shape sensing signals indicating the twist in the at least one optical fiber.

4. The system as recited in claim 2, wherein the motor is configured to be responsive to an imaging system, which indicates the twist in the at least one optical fiber.

5. The system as recited in claim 2, wherein the motor is configured to be responsive to a tracking system, which is independent from shape sensing using the optical shape sensing enabled device, the tracking system being employed to indicate the twist in the at least one optical fiber.

6. The system as recited in claim 1, wherein the rotation mechanism includes a motor configured to drive a transfer element to rotate the rotatable launch fixture.

7. The system as recited in claim 6, wherein the transfer element includes one of a belt, a wheel and a gear.

8. The system as recited in claim 1, further comprising a sensing device configured to measure rotation of the rotatable launch fixture.

9. A fiber twist reduction system for optical shape sensing enabled instruments, the system comprising:
    a rotatable launch fixture configured to hold a launch region of at least one optical fiber, the at least one optical fiber being disposed longitudinally along an optical shape sensing enabled device;
    a rotation mechanism coupled to the rotatable launch fixture and configured to rotate the launch region of the at least one optical fiber via the rotatable launch fixture; and
    a controller coupled to the rotation mechanism and configured to enable the rotation mechanism in response to a twist of the at least one optical fiber to rotate the launch region, at least reducing accumulated twist within the at least one optical fiber.

10. The system as recited in claim 9, wherein the rotation mechanism comprises a motor.

11. The system as recited in claim 10, wherein the motor is configured to drive a transfer element to rotate the rotatable launch fixture.

12. The system as recited in claim 11, wherein the transfer element includes one of a belt, a wheel and a gear.

13. The system as recited in claim 9, further comprising a sensing device configured to measure rotation of the rotatable launch fixture to update a coordinate system of the optical shape sensing enabled device.

14. The system as recited in claim 9, wherein the controller includes a shape reconstruction module configured to interpret shapes of the optical shape sensing enabled device and provide feedback on twist in the at least one optical fiber to enable the rotation of the launch region.

15. A method for reducing accumulated twist in an optical fiber for a shape sensing enabled device, the method comprising:
    providing a rotatable fiber launch fixture being configured to hold at least one optical fiber, an optical shape sensing enabled device including the at least one optical fiber disposed therein and a rotation mechanism configured to rotate the optical fiber disposed in the rotatable fiber launch fixture;
    measuring a twist in the at least one optical fiber disposed within the optical shape sensing enabled device; and
    in response to the measure twist, rotating the fiber launch fixture using the rotation mechanism to at least reduce accumulated twist within the at least one optical fiber.

* * * * *